United States Patent
Raymond et al.

(10) Patent No.: US 6,613,547 B1
(45) Date of Patent: Sep. 2, 2003

(54) PICHIA METHANOLICA GLYCERALDEHYDE-3-PHOSPHATE DEHYDROGENASE 1 PROMOTER AND TERMINATOR

(75) Inventors: Christopher K. Raymond, Seattle, WA (US); Erica Vanaja, Seattle, WA (US); Brady G. Miller, 2929 Kings Dr. #4308, Dallas, TX (US) 75219; James S. Sloan, 6423 NE. 154th St., Kenmore, WA (US) 98028

(73) Assignees: ZymoGenetics, Inc., Seattle, WA (US); Brady G. Miller, Dallas, TX (US); James S. Sloan, Kenmore, WA (US)

( * ) Notice: Subject to any disclaimer, the term of this patent is extended or adjusted under 35 U.S.C. 154(b) by 64 days.

(21) Appl. No.: 09/786,606

(22) PCT Filed: Jun. 16, 2000

(86) PCT No.: PCT/US00/16671

§ 371 (c)(1),
(2), (4) Date: Mar. 6, 2001

(87) PCT Pub. No.: WO00/78978

PCT Pub. Date: Dec. 28, 2000

Related U.S. Application Data

(60) Provisional application No. 60/140,703, filed on Jun. 24, 1999.

(51) Int. Cl.[7] .......................... C12P 21/02; C12N 1/19; C12N 15/11; C12N 15/63; C12N 15/81
(52) U.S. Cl. ................. 435/69.1; 435/245.23; 435/320.1; 536/24.1
(58) Field of Search ................. 536/24.1; 435/320.1, 435/69.1, 254.23

(56) References Cited

U.S. PATENT DOCUMENTS 6,258,559 B1 * 7/2001 Zamost ................. 435/69.1

FOREIGN PATENT DOCUMENTS

| WO | WO 97/17450 | * 5/1997 |
| WO | WO 98/20035 | * 5/1998 |

* cited by examiner

*Primary Examiner*—Terry McKelvey
(74) *Attorney, Agent, or Firm*—Brian J. Walsh; Gary E. Parker

(57) ABSTRACT

Transcription promoter and terminator sequences from the *Pichia methanolica* glyceraldehyde-3-phosphate dehydrogenase 1 gene (GAP1 gene) are disclosed. The sequences are useful within DNA constructs for the production of proteins of interest in cultured *P. methanolica* cells. Within the expression vectors, a GAP1 promoter and/or a GAP1 terminator is operably linked to a DNA segment encoding the protein of interest.

20 Claims, 2 Drawing Sheets

PICHIA METHANOLICA GLYCERALDEHYDE-3-PHOSPHATE DEHYDROGENASE 1 PROMOTER AND TERMINATOR

The present invention claims the benefit of U.S. Provisional Application Serial No. 60/140,703, filed Jun. 24, 1999, which is herein incorporated by reference.

BACKGROUND OF THE INVENTION

Methylotrophic yeasts are those yeasts that are able to utilize methanol as a sole source of carbon and energy. Species of yeasts that have the biochemical pathways necessary for methanol utilization are classified in four genera, Hansenula, Pichia, Candida, and Torulopsis. These genera are somewhat artificial, having been based on cell morphology and growth characteristics, and do not reflect close genetic relationships (Billon-Grand, *Mycotaxon* 35:201–204, 1989; Kurtzman, *Mycologia* 15 84:72–76, 1992). Furthermore, not all species within these genera are capable of utilizing methanol as a source of carbon and energy. As a consequence of this classification, there are great differences in physiology and metabolism between individual species of a genus.

Methylotrophic yeasts are attractive candidates for use in recombinant protein production systems for several reasons. First, some methylotrophic yeasts have been shown to grow rapidly to high biomass on minimal defined media. Second, recombinant expression cassettes are genomically integrated and therefore mitotically stable. Third, these yeasts are capable of secreting large amounts of recombinant proteins. See, for example, Faber et al., *Yeast* 11:1331, 1995; Romanos et al., *Yeast* 8:423, 1992; Cregg et al., *Bio/Technology* 11:905, 1993; U.S. Pat. No. 4,855,242; U.S. Pat. No. 4,857,467; U.S. Pat. No. 4,879,231; and U.S. Pat. No. 4,929,555; and Raymond, U.S. Pat. Nos. 5,716,808, 5,736,383, 5,854,039, and 5,888,768.

Previously described expression systems for methylotrophic yeasts rely largely on the use of methanol-inducible transcription promoters. The use of methanol-induced promoters is, however, problematic as production is scaled up to commercial levels. The overall volume of methanol used during the fermentation process can be as much as 40% of the final fermentation volume, and at 1000-liter fermentation scale and above the volumes of methanol required for induction necessitate complex and potentially expensive considerations.

There remains a need in the art for additional materials and methods to enable the use of methylotrophic yeasts for production of polypeptides of economic importance, including industrial enzymes and pharmaceutical proteins. The present invention provides such materials and methods as well as other, related advantages.

SUMMARY OF THE INVENTION

Within one aspect, the present invention provides an isolated DNA molecule of up to 1500 nucleotides in length comprising nucleotide 810 to nucleotide 1724 of SEQ ID NO:1.

Within a second aspect of the invention there is provided a DNA construct comprising the following operably linked elements: a first DNA segment comprising at least a portion of the sequence of SEQ ID NO: 1 from nucleotide 733 to nucleotide 1732, wherein the portion is a functional transcription promoter; a second DNA segment encoding a protein of interest other than a *Pichia methanolica* glyceraldehyde-3-phosphate dehydrogenase; and a third DNA segment comprising a transcription terminator. Within one embodiment, the first DNA segment is from 900 to 1500 nucleotides in length. Within another embodiment, the first DNA segment is from 900 to 1000 nucleotides in length. Within a further embodiment, the first DNA segment comprises nucleotide 810 to nucleotide 1724 of SEQ ID NO:1. Within an additional embodiment, the first DNA segment is essentially free of DNA encoding a *P. methanolica* glyceraldehyde-3-phosphate dehydrogenase. The DNA construct may further comprise a selectable marker, such as a *P. methanolica* gene, for example a *P. methanolica* ADE2 gene. The DNA construct may be a closed, circular molecule or a linear molecule. Within other embodiments, the DNA constuct further comprises a secretory signal sequence, such as a *Saccharomyces cerevisiae* alpha-factor pre-pro sequence, operably linked to the first and second DNA segments. Within additional embodiments, the third DNA segment comprises a transcription terminator of a *P. methanolica* AUG1 or GAP1 gene.

Within a third aspect of the invention there is provided a *P. methanolica* cell containing a DNA construct as disclosed above. Within one embodiment, the DNA construct is genomically integrated. Within a related embodiment, the DNA construct is genomically integrated in multiple copies. Within a further embodiment, the *P. methanolica* cell is functionally deficient in vacuolar proteases proteinase A and proteinase B.

Within a fourth aspect of the invention there is provided a method of producing a protein of interest comprising the steps of (a) culturing a *P. methanolica* cell as disclosed above whereby the second DNA segment is expressed and the protein of interest is produced, and (b) recovering the protein of interest.

Within a fifth aspect of the invention there is provided a DNA construct comprising the following operably linked elements: a first DNA segment comprising a *P. methanolica* gene transcription promoter; a second DNA segment encoding a protein of interest other than a *P. methanolica* protein; and a third DNA segment comprising nucleotides 2735 to 2795 of SEQ ID NO: 1.

These and other aspects of the invention will become evident upon reference to the following detailed description of the invention and the attached drawings.

DETAILED DESCRIPTION OF THE INVENTION

Figure 1:
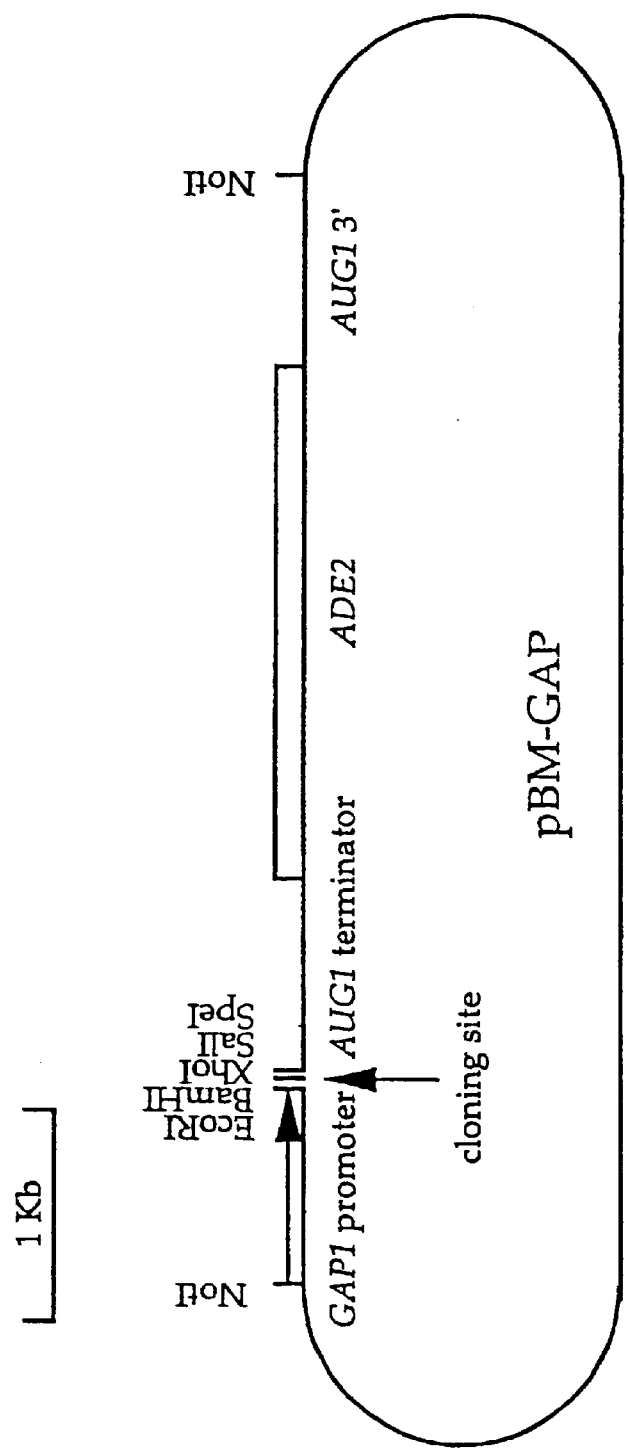
FIG. 1 illustrates the vector pBM/GAP, comprising the *P. methanolica* GAP1 promoter.

The term "allelic variant" is used herein to denote an alternative form of a gene. Allelic variation is known to exist in populations and arises through mutation.

A "DNA construct" is a DNA molecule, either single- or double-stranded, that has been modified through human intervention to contain segments of DNA combined and juxtaposed in an arrangement not existing in nature.

A "DNA segment" is a portion of a larger DNA molecule having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "functionally deficient" denotes the expression in a cell of less than 10% of an activity as compared to the level of that activity in a wild-type counterpart. Often the expression level will be less than 1% of the activity in the wild-type counterpart, frequently less than 0.01% as determined by appropriate assays. In some instances it is desirable that the activity be essentially undetectable (i.e., not significantly above background). Functional deficiencies in genes can be generated by mutations in either coding or non-coding regions.

The term "gene" is used herein to denote a DNA segment encoding a polypeptide. Where the context allows, the term includes genomic DNA (with or without intervening sequences), cDNA, and synthetic DNA. Genes may include non-coding sequences, including promoter elements.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones.

"Operably linked", when referring to DNA segments, indicates that the segments are arranged so that they function in concert for their intended purposes, e.g., transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When these terms are applied to double-stranded molecules they are used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes. Sequences within promoters that function in the initiation of transcription are often characterized by consensus nucleotide sequences. These promoter elements include RNA polymerase binding sites, TATA sequences, and transcription factor binding sites. Of particular interest within the present invention are Gcr1p binding sites, characterized by the consensus sequences CTTCC or GGAAG, and Rap1p binding sites. See, in general, Watson et al., eds., *Molecular Biology of the Gene,* 4th ed., The Benjamin/Cummings Publishing Company, Inc., Menlo Park, Calif. 1987.

A "pro sequence" is a DNA sequence that commonly occurs immediately 5' to the mature coding sequence of a gene encoding a secretory protein. The pro sequence encodes a pro peptide that serves as a cis-acting chaperone as the protein moves through the secretory pathway.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are commonly defined in terms of their amino acid backbone structures; substituents such as carbohydrate groups are generally not specified, but may be present nonetheless.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway. A secretory peptide and a pro peptide may be collectively referred to as a pre-pro peptide.

The present invention provides isolated DNA molecules comprising a *Pichia methanolica* glyceraldehyde-3-phosphate dehydrogenase (GAPDH) gene promoter. The invention also provides isolated DNA molecules comprising a *P. methanolica* GAPDH gene terminator. The promoter and terminator can be used within methods of producing proteins of interest, including proteins of pharmaceutical or industrial value.

The sequence of a DNA molecule comprising a *P. methanolica* glyceraldehyde-3-phosphate dehydrogenase (GAPDH) gene promoter, coding region, and terminator is shown in SEQ ID NO: 1. The gene has been designated GAP1. those skilled in the art will recognize that SEQ ID NO:1 represents a single allele of the *P. methanolica* GAP1 gene and that other functional alleles (allelic variants) are likely to exist, and that allelic variation may include nucleotide changes in the promoter region, coding region, or terminator region.

Within SEQ ID NO: 1, the GAPDH open reading frame begins with the methionine codon (ATG) at nucleotides 1733–1735. The transcription promoter is located upstream of the ATG. Gene expression experiments showed that a functional promoter was contained within the ca. 900 nucleotide 5'-flanking region of the GAP1 gene. Analysis of this promoter sequence revealed the presence of a number of sequences homologous to *Saccharomyces cerevisiae* promoter elements. These sequences include a concensus TATAAA box at nucleotides 1584 to 1591, a consensus Rap1p binding site (Graham and Chambers, *Nuc. Acids Res.* 22:124–130, 1994) at nucleotides 1355 to 1367, and potential Gcr1p binding sites (Shore, *Trends Genet.* 10:408–412, 1994) at nucleotides 1225 to 1229, 1286 to 1290, 1295 to 1299, 1313 to 1317, 1351 to 1354, 1370 to 1374, 1389 to 1393, and 1457 to 1461. While not wishing to be bound by theory, it is believed that these sequences may perform functions similar to those of their counterparts in the *S. cerevisiae* TDH3 promoter (Bitter et al., *Mol. Gen. Genet.* 231:22–32, 1991), that is, they may bind the homologous transcription regulatory elements. Mutation of the region around the consensus Gcr1p binding site in the *P. methanolica* GAP1 promoter has been found to destroy promoter activity.

Preferred portions of the sequence shown in SEQ ID NO:1 for use within the present invention as transcription promoters include segments comprising at least 900 contiguous nucleotides of the 5' non-coding region of SEQ ID NO:1, and preferably comprising nucleotide 810 to nucleotide 1724 of the sequence shown in SEQ ID NO:1. Those skilled in the art will recognize that longer portions of the 5' non-coding region of the P. methanolica GAP1 gene can also be used. Promoter sequences of the present invention can thus include the sequence of SEQ ID NO:1 through nucleotide 1732 in the 3' direction and can extend to or beyond nucleotide 232 in the 5' direction. For convenience and ease of manipulation, the promoter used within an expression DNA construct will generally not exceed 1.5 kb in length, and will often not exceed 1.0 kb in length.

As disclosed in more detail in the examples that follow, the sequence of SEQ ID NO:1 from nucleotide 810 to 1724 provides a functional transcription promoter. However, additional nucleotides can be removed from either or both ends of this sequence and the resulting sequence tested for promoter function by joining it to a sequence encoding a protein, preferably a protein for which a convenient assay is readily available.

Within the present invention it is preferred that the GAP1 promoter be substantially free of GAP1 gene coding sequence, which begins with nucleotide 1733 in SEQ ID NO: 1. As used herein, the term "substantially free of GAP1 gene coding sequence" means that the promoter DNA includes not more than 15 nucleotides of the GAP1 coding sequences, preferably not more than 10 nucleotides, and more preferably not more than 3 nucleotides. Within one embodiment of the invention, the GAP1 promoter is provided free of coding sequence of the P. methanolica GAP1 gene. However, those skilled in the art will recognize that a GAP1 gene fragment that includes the initiation ATG (nucleotides 1733 to 1735) of SEQ ID NO: 1 can be operably linked to a heterologous coding sequence that lacks an ATG, with the GAP1 ATG providing for initiation of translation of the heterologous sequence. Those skilled in the art will further recognize that additional GAP1 coding sequences can also be included, whereby a fusion protein comprising GAP1 and heterologous amino acid sequences is produced. Such a fusion protein may comprise a cleavage site to facilitate separation of the GAP1 and heterologous sequences subsequent to translation.

In addition to the GAP1 promoter sequence, the present invention also provides transcription terminator sequences derived from the 3' non-coding region of the P. methanolica GAP1 gene. A consensus transcription termination sequence (Chen and Moore, Mol. Cell. Biol. 12:3470–3481, 1992) is at nucleotides 2774 to 2787 of SEQ ID NO:1. Within the present invention, there are thus provided transcription terminator gene segments of at least about 60 bp in length. Longer segments, for example at least 90 bp in length or about 200 bp in length, will often be used. These segments comprise the termination sequence disclosed above, and may have as their 5' termini nucleotide 2735 of SEQ ID NO:1. Those skilled in the art will recognize, however, that the transcription terminator segment that is provided in an expression vector can include at its 5' terminus the TAA translation termination codon at nucleotides 2732–2734 of SEQ ID NO: 1 to permit the insertion of coding sequences that lack a termination codon.

Techniques for manipulating cloned DNA molecules and introducing exogenous DNA into a variety of host cells are well known in the art and are disclosed by, for example, Sambrook et al., *Molecular Cloning: A Laboratory Manual*, 2nd ed., Cold Spring Harbor Laboratory Press, Cold Spring Harbor, N.Y., 1989; Murray, ed., Gene Transfer and Expression Protocols, Humana Press, Clifton, N.J., 1991; Glick and Pasternak, *Molecular Biotechnology: Principles and Applications of Recombinant DNA*, ASM Press, Washington, D.C., 1994; Ausubel et al. (eds.), *Short Protocols in Molecular Biology*, 3rd edition, John Wiley and Sons, Inc., N.Y., 1995; Wu et al., *Methods in Gene Biotechnology*, CRC Press, N.Y., 1997. DNA vectors, including expression vectors, commonly contain a selectable marker and origin of replication that function in a bacterial host (e.g., E. coli) to permit the replication and amplification of the vector in a prokaryotic host. If desired, these prokaryotic elements can be removed from a vector before it is introduced into an alternative host. For example, such prokaryotic sequences can be removed by linearization of the vector prior to its introduction into a P. methanolica host cell.

Within one embodiment of the invention, expression vectors are provided that comprise a first DNA segment comprising at least a portion of the sequence of SEQ ID NO: I that is a functional transcription promoter operably linked to a second DNA segment encoding a protein of interest. When it is desired to secrete the protein of interest, the vector will further comprise a secretory signal sequence operably linked to the first and second DNA segments. The secretory signal sequence may be that of the protein of interest, or may be derived from another secreted protein, preferably a secreted yeast protein. A preferred such yeast secretory signal sequence is the S. cerevisiae alpha-factor (MFα1) pre-pro sequence (disclosed by Kurjan et al., U.S. 5 Patent No. 4,546,082 and Brake, U.S. Pat. No. 4,870,008).

Within other embodiments of the invention, expression vectors are provided that comprise a DNA segment comprising a portion of SEQ ID NO: 1 that is a functional transcription terminator operably linked to an additional DNA segment encoding a protein of interest. Within one embodiment, the P. methanolica GAP1 promoter and terminator sequences are used in combination, wherein both are operably linked to a DNA segment encoding a protein of interest within an expression vector.

Expression vectors of the present invention further comprise a selectable marker to permit identification and selection of P. methanolica cells containing the vector. Selectable markers provide for a growth advantage of cells containing them. The general principles of selection are well known in the art. The selectable marker is preferably a P. methanolica gene. Commonly used selectable markers are genes that encode enzymes required for the synthesis of amino acids or nucleotides. Cells having mutations in these genes cannot grow in media lacking the specific amino acid or nucleotide unless the mutation is complemented by the selectable marker. Use of such "selective" culture media ensures the stable maintenance of the heterologous DNA within the host cell. An exemplary selectable marker of this type for use in P. methanolica is a P. methanolica ADE2 gene, which encodes phosphoribosyl-5-aminoimidazole carboxylase (AIRC; EC 4.1.1.21). See, Raymond, U.S. Pat. No. 5,736, 383. The ADE2 gene, when transformed into an ade2 host cell, allows the cell to grow in the absence of adenine. The coding strand of a representative P. methanolica ADE2 gene sequence is shown in SEQ ID NO:2. The sequence illustrated includes 1006 nucleotides of 5' non-coding sequence and 442 nucleotides of 3' non-coding sequence, with the initiation ATG codon at nucleotides 1007–1009. Within one embodiment of the invention, a DNA segment comprising nucleotides 407-2851 is used as a selectable marker, although longer or shorter segments could be used as long as the coding portion is operably linked to promoter and terminator sequences. In the alternative, a dominant selectable marker, which provides a growth advantage to wild-type cells, may be used. Typical dominant selectable markers are genes that provide resistance to antibiotics, such as neomycin-type antibiotics (e.g., G418), hygromycin B, and bleomycin/phleomycin-type antibiotics (e.g., Zeocin™; available from Invitrogen Corporation, San Diego, Calif.). An exemplary dominant selectable marker for use in *P. methanolica* is the Sh bla gene, which inhibits the activity of Zeocin™.

The use of *P. methanolica* cells as a host for the production of recombinant proteins is disclosed in WIPO Publications WO 97/17450, WO 97/17451, WO 98/02536, and WO 98/02565; and U.S. Pat. Nos. 5,716,808, 5,736,383, 5,854,039, and 5,888,768. Expression vectors for use in transforming *P. methanolica* will commonly be prepared as double-stranded, circular plasmids, which are preferably linearized prior to transformation. To facilitate integration of the expression vector DNA into the host chromosome, the entire expression segment of the plasmid can be flanked at both ends by host DNA sequences (e.g., AUG1 3' sequences). Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Integrative transformants are preferred for use in protein production processes. Such cells can be propagated without continuous selective pressure because DNA is rarely lost from the genome. Integration of DNA into the host chromosome can be confirmed by Southern blot analysis. Briefly, transformed and untransformed host DNA is digested with restriction endonucleases, separated by electrophoresis, blotted to a support membrane, and probed with appropriate host DNA segments. Differences in the patterns of fragments seen in untransformed and transformed cells are indicative of integrative transformation. Restriction enzymes and probes can be selected to identify transforming DNA segments (e.g., promoter, terminator, heterologous DNA, and selectable marker sequences) from among the genomic fragments.

Differences in expression levels of heterologous proteins can result from such factors as the site of integration and copy number of the expression cassette among individual isolates. It is therefore advantageous to screen a number of isolates for expression level prior to selecting a production strain. Isolates exhibiting a high expression level will commonly contain multiple integrated copies of the desired expression cassette. A variety of suitable screening methods are available. For example, transformant colonies are grown on plates that are overlayed with membranes (e.g., nitrocellulose) that bind protein. Proteins are released from the cells by secretion or following lysis, and bind to the membrane. Bound protein can then be assayed using known methods, including immunoassays. More accurate analysis of expression levels can be obtained by culturing cells in liquid media and analyzing conditioned media or cell lysates, as appropriate. Methods for concentrating and purifying proteins from media and lysates will be determined in part by the protein of interest. Such methods are readily selected and practiced by the skilled practitioner.

For production of secreted proteins, host cells having functional deficiencies in the vacuolar proteases proteinase A, which is encoded by the PEP4 gene, and proteinase B, which is encoded by the PRB1 gene, can be used to minimize spurious proteolysis. Vacuolar protease activity (and therefore vacuolar protease deficiency) is measured using any of several known assays, such as those developed for *S. cerevisiae* and disclosed by Jones, *Methods Enzymol.* 194:428–453, 1991. One such assay is the APNE overlay assay, which detects activity of carboxypeptidase Y (CpY). See, Wolf and Fink, *J. Bact.* 123:1150–1156, 1975. Because the zymogen (pro)CpY is activated by proteinase A and proteinase B, the APNE assay is indicative of vacuolar protease activity in general. The APNE overlay assay detects the carboxypeptidase Y-mediated release of β-naphthol from N-acetyl-phenylalanine-β-naphthyl-ester (APNE), which results in the formation of an insoluble red dye by the reaction of the β-naphthol with the diazonium salt Fast Garnet GBC. Cells growing on assay plates (e.g., YEPD plates) at room temperature are overlayed with 8 ml RxM. RxM is prepared by combining 0.175 g agar, 17.5 ml $H_2O$, and 5 ml 1 M Tris-HCl pH 7.4, microwaving the mixture to dissolve the agar, cooling to ~55° C., adding 2.5 ml freshly made APNE (2 mg/ml in dimethylformamide) (Sigma Chemical Co., St. Louis, Mo.), and, immediately before assay, 20 mg Fast Garnet GBC salt (Sigma Chemical Co.). The overlay is allowed to solidify, and color development is observed. Wild-type colonies are red, whereas CPY deletion strains are white. Carboxypeptidase Y activity can also be detected by the well test, in which cells are distributed into wells of a microtiter test plate and incubated in the presence of N-benzoyl-L-tyrosine p-nitroanilide (BTPNA) and dimethylformamide. The cells are permeabilized by the dimethylformamide, and CpY in the cells cleaves the amide bond in the BTPNA to give the yellow product p-nitroaniline. Assays for CpY will detect any mutation that reduces protease activity so long as that activity ultimately results in the reduction of CpY activity.

*P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A suitable culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine, 0.006% L-leucine).

For large-scale culture, one to two colonies of a *P. methanolica* strain can be picked from a fresh agar plate (e.g., YEPD agar) and suspended in 250 ml of YEPD broth contained in a two-liter baffled shake flask. The culture is grown for 16 to 24 hours at 30° C. and 250 rpm shaking speed. Approximately 50 to 80 milliliters of inoculum are used per liter starting fermentor volume (5–8% v/v inoculum).

A preferred fermentation medium is a soluble medium comprising glucose as a carbon source, inorganic ammonia, potassium, phosphate, iron, and citric acid. As used herein, a "soluble medium" is a medium that does not contain visible precipitation. Preferably, the medium lacks phosphate glass (sodium hexametaphosphate). A preferred medium is prepared in deionized water and does not contain calcium sulfate. As a minimal medium, it is preferred that the medium lacks polypeptides or peptides, such as yeast extracts. However, acid hydrolyzed casein (e.g., casamino acids or amicase) can be added to the medium if desired. An illustrative fermentation medium is prepared by mixing the following compounds: $(NH_4)_2SO_4$ (11.5 grams/liter), $K_2HPO_4$ (2.60 grams/liter), $KH_2PO_4$ (9.50 grams/liter), $FeSO_4 \cdot 7H_2O$ (0.40 grams/liter), and citric acid (1.00 gram/liter). After adding distilled, deionized water to one liter, the solution is sterilized by autoclaving, allowed to cool, and then supplemented with the following: 60% (w/v) glucose solution (47.5 milliliters/liter), 10× trace metals solution (20.0 milliliters/liter), 1 M MgSO$_4$ (20.0 milliliters/liter), and vitamin stock solution (2.00 milliliters/liter). The 10× trace metals solution contains FeSO$_4$•7H$_2$O (100 mM), CuSO$_4$•5H$_2$O (2 mM), ZnSO$_4$•7H$_2$O (8 mM), MnSO$_4$•H$_2$O (8 mM), CoCl$_2$•6H$_2$O (2 mM), Na$_2$MoO$_4$•2H$_2$O (1 mM), H$_3$BO$_3$ (8 mM), KI (0.5 mM), NiSO$_4$•6H$_2$O (1 mM), thiamine (0.50 grams/liter), and biotin (5.00 milligrams/liter). The vitamin stock solution contains inositol (47.00 grams/liter), pantothenic acid (23.00 grams/liter), pyrodoxine (1.20 grams/liter), thiamine (5.00 grams/liter), and biotin (0.10 gram/liter). Those of skill in the art can vary these particular ingredients and amounts. For example, ammonium sulfate can be substituted with ammonium chloride, or the amount of ammonium sulfate can be varied, for example, from about 11 to about 22 grams/liter.

After addition of trace metals and vitamins, the pH of the medium is typically adjusted to pH 4.5 by addition of 10% H$_3$PO$_4$. Generally, about 10 milliliters/liter are added, and no additional acid addition will be required. During fermentation, the pH is maintained between about 3.5 to about 5.5, or about 4.0 to about 5.0, depending on protein produced, by addition of 5 N NH$_4$OH.

An illustrative fermentor is a BIOFLO 3000 fermentor system (New Brunswick Scientific Company, Inc.; Edison, N.J.). This fermentor system can handle either a six-liter or a fourteen-liter fermentor vessel. Fermentations performed with the six-liter vessel are prepared with three liters of medium, whereas fermentations performed with the fourteen-liter vessel are prepared with six liters of medium. The fermentor vessel operating temperature is typically set to 30° C. for the course of the fermentation, although the temperature can range between 27–31° C. depending on the protein expressed. The fermentation is initiated in a batch mode. The glucose initially present is often used by approximately 10 hours elapsed fermentation time (EFT), at which time a glucose feed can be initiated to increase the cell mass. An illustrative glucose feed contains 900 milliliters of 60% (w/v) glucose, 60 milliliters of 50% (w/v) (NH$_4$)$_2$SO$_4$, 60 milliliters of 10× trace metals solution, and 30 milliliters of 1 M MgSO$_4$. P. methanolica fermentation is robust and requires high agitation, aeration, and oxygen sparging to maintain the percentage dissolved oxygen saturation above 30%. The percentage dissolved oxygen should not drop below 15% for optimal expression and growth. The biomass typically reaches about 30 to about 80 grams dry cell weight per liter at 48 hours EFT.

Proteins produced according to the present invention are recovered from the host cells using conventional methods. If the protein is produced intracellulary, the cells are harvested (e.g., by centrifugation) and lysed to release the cytoplasmic contents. Methods of lysis include enzymatic and mechanical disruption. The crude extract is then fractionated according to known methods, the specifics of which will be determined for the particular protein of interest. Secreted proteins are recovered from the conditioned culture medium using standard methods, also selected for the particular protein. See, in general, Scopes, *Protein Purification: Principles and Practice*, Springer-Verlag, N.Y., 1994.

The materials and methods of the present invention can be used to produce proteins of research, industrial, or pharmaceutical interest. Such proteins include enzymes, such as lipases, cellulases, and proteases; enzyme inhibitors, including protease inhibitors; growth factors such as platelet derived growth factor (PDGF), fibroblast growth factors (FGF), epidermal growth factor (EGF), vascular endothelial growth factors (VEGFs); glutamic acid decarboxylase (GAD); cytokines, such as erythropoietin, thrombopoietin, colony stimulating factors, interleukins, and interleukin antagonists; hormones, such as insulin, proinsulin, leptin, and glucagon; and receptors, including growth factor receptors, which can be expressed in truncated form ("soluble receptors") or as fusion proteins with, for example, immunoglobulin constant region sequences. DNAs encoding these and other proteins are known in the art. See, for example, U.S. Pat. Nos. 4,889,919; 5,219,759; 4,868,119; 4,968,607; 4,599,311;. 4,784,950; 5,792,850; 5,827,734; 4,703,008; 4,431,740; and 4,762,791; and WIPO Publications WO 95/21920 and WO 96/22308.

The materials and methods of the present invention can be used to produce unglycosylated pharmaceutical proteins. Yeast cells, including P. methanolica cells, produce glycoproteins with carbohydrate chains that differ from their mammalian counterparts. Mammalian glycoproteins produced in yeast cells may therefore be regarded as "foreign" when introduced into a mammal, and may exhibit, for example, different pharmacokinetics than their naturally glycosylated counterparts.

The invention is further illustrated by the following, non-limiting examples.

EXAMPLES

EXAMPLE 1

To clone the P. methanolica GAP1 gene, sense (ZC11,356; SEQ ID NO:3) and antisense (ZC11,357; SEQ ID NO:4) PCR primers were designed from an alignment of the coding regions of GAPDH genes of Saccharomyces cerevisiae, Kluyveromyces lactis, and mouse. The primers were then used to amplify P. methanolica genomic DNA. An amplified sequence 608 bp long was recovered and was found to have 78.1% homology to the corresponding S. cerevisiae GAPDH gene sequence.

A P. methanolica genomic library was constructed in the vector pRS426 (Christianson et al., *Gene* 110:119–122, 1992), a shuttle vector comprising 2μg and S. cerevisiae URA3 sequences, allowing it to be propagated in S. cerevisiae. Genomic DNA was prepared from strain CBS6515 according to standard procedures. Briefly, cells were cultured overnight in rich media, spheroplasted with zymolyase, and lysed with SDS. DNA was precipitated from the lysate with ethanol and extracted with a phenol/chloroform mixture, then precipitated with ammonium acetate and ethanol. Gel electrophoresis of the DNA preparation showed the presence of intact, high molecular weight DNA and appreciable quantities of RNA. The DNA was partially digested with Sau 3A by incubating the DNA in the presence of a dilution series of the enzyme. Samples of the digests were analyzed by electrophoresis to determine the size distribution of fragments. DNA migrating between 4 and 12 kb was cut from the gel and extracted from the gel slice. The size-fractionated DNA was then ligated to pRS426 that had been digested with Bam HI and treated with alkaline phosphatase. Aliquots of the reaction mixture were electroporated into E. coli MC1061 cells using an electroporator (Gene Pulser™; BioRad Laboratories, Hercules, Calif.) as recommended by the manufacturer.

The library was screened by PCR using sense (ZC11,733; SEQ ID NO:5) and antisense (ZC11,734; SEQ ID NO:6) primers designed from the sequenced region of the P. methanolica GAPDH gene fragment. The PCR reaction mixture was incubated for one minute at 94° C.; followed by 34 cycles of 94° C., one minute, 52° C., 45 seconds, 72° C., two minutes; and a termination cycle of 94° C., one minute, 54° C., one minute, 72° C., eleven minutes. Starting with 43 library pools, positive pools were identified and broken down to individual colonies. A single colony with a pRS426 plasmid containing the *P. methanolica* GAPDH gene as its insert was isolated. The orientation of the GAPDH gene and the length of the 5' and 3' flanking sequences in the insert were deduced by DNA sequencing (SEQ ID NO:1). This gene was designated GAP1.

A plasmid containing the GAP1 gene, designated pGAPDH, has been deposited as an *E. coli* strain MC1061 transformant with American Type Culture Collection, Manassas, Va. under the terms of the Budapest Treaty. The deposited strain has been assigned the designation PTA-3 and a deposit date of May 4, 1999.

EXAMPLE 2

The cloned *P. methanolica* GAP1 promoter was used to construct an expression cassette by replacing the AUG1 promoter in the vector pCZR133 (disclosed in U.S. Pat. No. 5,736,383). Plasmid pCZR133 comprises the *P. methanolica* AUG1 promoter and terminator flanking a multiple cloning site, and a *P. methanolica* ADE2 selectable marker. The GAP1 promoter (nucleotides 810 to 1724 of SEQ ID NO:1) was amplified by PCR using primers that introduced a Not I site at the 5' end (SEQ ID NO:7; ZC12,586), and Eco RI and Bam HI sites at the 3' end (SEQ ID NO:8;

ZC12,565). The reaction mixture was incubated for one minute at 94° C.; followed by 34 cycles of 94° C., one minute, 52° C., one minute, 72° C., three minutes; and a termination cycle of 94° C., one minute, 54° C., seven minutes, 72° C., 23 minutes. The amplified promoter was then blunt-end ligated into a phagemid vector (pBluescript®; Stratagene, La Jolla, Calif.). The orientation of the promoter in the vector was determined by restriction analysis. The promoter was isolated as a Not I and Bam HI fragment. Plasmid pCZR133 was digested with Not I and Bam HI, and the digest was electrophoresed on a gel. Two fragments, the Ade2/termination fragment and the pUC fragment, were recovered. The pUC fragment was dephosphorylated. The two vector fragments and the promoter were joined in a three-part ligation. The resulting plasmid was designated pBM/GAP (FIG. 1).

Figure 2:
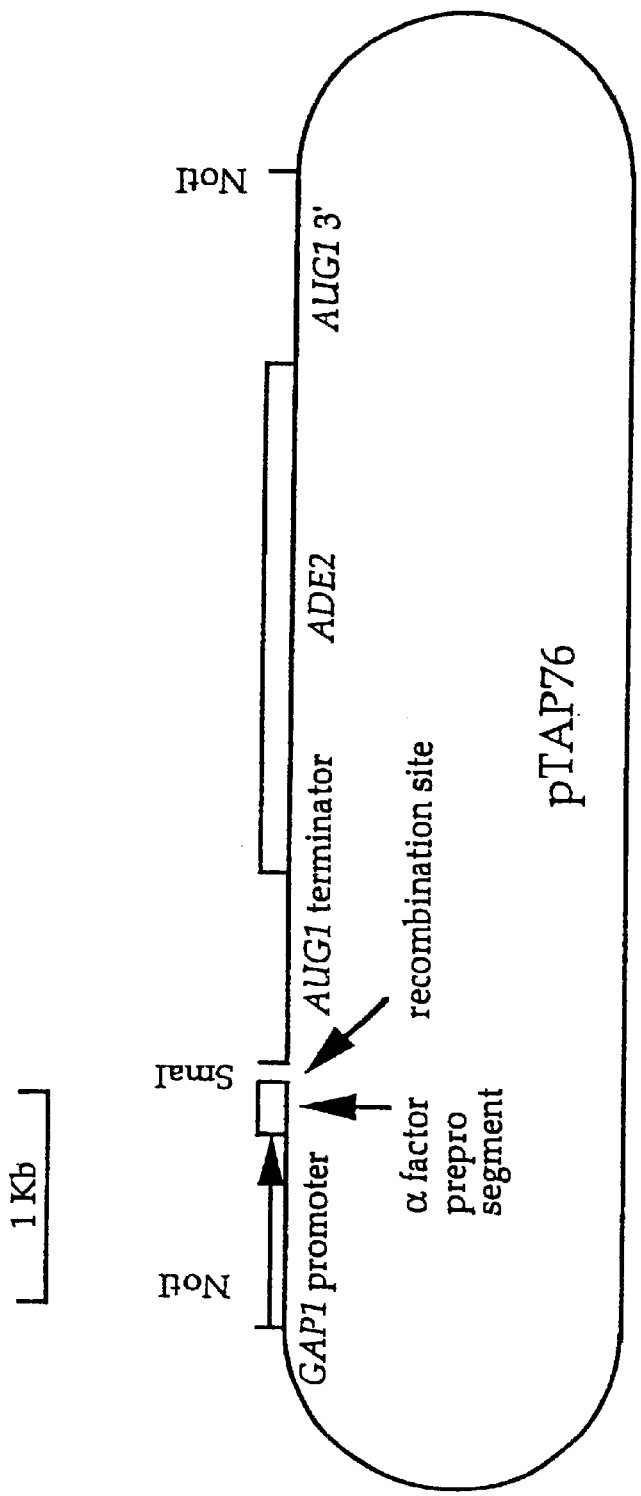
FIG. 2 illustrates the vector pTAP76.

A second vector, pTAP76 (FIG. 2) was constructed. This vector comprises the GAP1 promoter, α-factor prepro sequence, a SmaI cleavage site, the AUG1 terminator, the ADE2 selectable marker, and AUG1 3' non-coding sequence cloned into a pRS316 (Sikorski and Hieter, *Genetics* 122:19–27, 1989) backbone. The pTAP76 vector is linearized at the SmaI site and combined with a DNA fragment of interest and double-stranded recombination linkers in *S. cerevisiae*, whereby the fragment of interest is joined to the vector by homologous recombination as disclosed by Raymond et al., *BioTechniques* 26:134–141, 1999.

EXAMPLE 3

Expression of heterologous genes from the GAP1 promoter was tested using LacZ and GFP (green fluorescent protein) reporter genes. These genes were prepared as Eco RI-Bam HI fragments, and were individually ligated to Eco RI, Bam HI-digested pBM/GAP. The resulting plasmids were transformed into *P. methanolica* host cells, and the cells were grown in both glucose and methanol fermentation conditions. Both reporter genes were expressed under both conditions, showing that the cloned GAP1 promoter can be used to constitutively express heterologous genes in *P. methanolica* cells.

EXAMPLE 4

To generate a *P. methanolica* strain deficient for vacuolar proteases, the PEP4 and PRB1 genes were identified and disrupted. PEP4 and PRB1 sequences were amplified by PCR in reaction mixtures containing 100 pmol of primer DNA, 1X buffer as supplied (Boehringer Mannheim, Indianapolis, Ind.), 250 µM dNTPs, 1–100 pmol of template DNA, and 1 unit of Taq polymerase in a reaction volume of 100 µl. The DNA was amplified over 30 cycles of 94° C., 30 seconds; 50° C., 60 seconds; and 72° C., 60 seconds.

Using an alignment of PEP4 sequences derived from *S. cerevisiae* (Ammerer et al., *Mol. Cell. Biol.* 6:2490–2499, 1986; Woolford et al., *Mol. Cell. Biol.* 6:2500–2510, 1986) and *P. pastoris* (Gleeson et al., U.S. Pat. No. 5,324,660), several sense and antisense primers corresponding to conserved regions were designed. One primer set, ZC9118 (SEQ ID NO:9) and ZC9464 (SEQ ID NO:10) produced a PCR product of the expected size from genomic DNA, and this set was used to identify a genomic clone corresponding to the amplified region. DNA sequencing of a portion of this genomic clone (shown in SEQ ID NO:11) revealed an open reading frame encoding a polypeptide (SEQ ID NO: 12) with 70% amino acid identity with proteinase A from *S. cerevisiae*.

Primers for the identification of *P. methanolica* PRB1 were designed on the basis of alignments between the PRB1 genes of *S. cerevisiae* (Moehle et al., *Mol. Cell. Biol.* 7:4390–4399, 1987), *P. pastoris* (Gleeson et al., U.S. Pat. No. 5,324,660), and *Kluyveromyces lactis* (Fleer et al., WIPO Publication WO 94/00579). One primer set, ZC9126 (SEQ ID NO:13) and ZC9741 (SEQ ID NO:14) amplified a ca. 400 bp fragment from genomic DNA (SEQ ID NO: 15). This product was sequenced and found to encode a polypeptide (SEQ ID NO: 16) with 70% amino acid identity with proteinase B from *S. cerevisiae*. The PRB primer set was then used to identify a genomic clone encompassing the *P. methanolica* PRB1 gene.

Deletion mutations in the *P. methanolica* PEP4 and PRB1 genes were generated using available restriction enzyme sites. The cloned genes were restriction mapped. The pep4Δ allele was created by deleting a region of approximately 500 bp between BamHI and NcoI sites and including nucleotides 1 through 393 the sequence shown in SEQ ID NO: 11. The prb1Δ allele was generated by deleting a region of approximately 1 kbp between NcoI and EcoRV sites and including the sequence shown in SEQ ID NO:15. The cloned PEP4 and PRB1 genes were subcloned into pCZR139, a phagemid vector (pBluescript® II KS(+), Stratagene, La Jolla, Calif.) that carried a 2.4 kb SpeI ADE2 insert, to create the deletions. In the case of PEP4 gene, the unique BamHI site in pCZR139 was eliminated by digestion, fill-in, and religation. The vector was then linearized by digestion with EcoRI and HindIII, and a ca. 4 kb EcoRI—HindIII fragment spanning the PEP4 gene was ligated to the linearized vector to produce plasmid pCZR142. A ca. 500-bp deletion was then produced by digesting pCZR142 with BamHI and NcoI, filling in the ends, and religating the DNA to produce plasmid pCZR143. The PRBI gene (~5 kb XhoI—BamHI fragment) was subcloned into pCZR139, and an internal EcoRV—NcoI fragment, comprising the sequence shown in SEQ ID NO:15, was deleted to produce plasmid pCZR153.

Plasmid pCZR143 was linearized with Asp718, which cut at a unique site. The linearized plasmid was introduced into the *P. methanolica* PMAD11 strain (an ade2 mutant generated as disclosed in U.S. Pat. No. 5,736,383). Transformants were grown on ADE DS (Table 1) to identify Ade+ transformants. Two classes of white, Ade+ transformants were analyzed. One class arose immediately on the primary transformation plate; the second became evident as rapidly growing white papillae on the edges of unstable, pink transformant colonies.

Table 1

ADE DS 0.056% -Ade -Trp -Thr powder 0.67% yeast nitrogen base without amino acids 2% D-glucose 0.5% 200X tryptophan, threonine solution 18.22% D-sorbitol -Ade -Trp -Thr powder powder made by combining 3.0 g arginine, 5.0 g aspartic acid, 2.0 g histidine, 6.0 g isoleucine, 8.0 g leucine, 4.0 g lysine, 2.0 g methionine, 6.0 g phenylalanine, 5.0 g serine, 5.0 g tyrosine, 4.0 g uracil, and 6.0 g valine (all L-amino acids)

200X tryptophan, threonine solution 3.0% L-threonine, 0.8% L-tryptophan in $H_2O$ For plates, add 1.8% Bacto™ agar (Difco Laboratories)

Southern blotting was used to identify transformants that had undergone the desired homologous integration event. 100 μl of cell paste was scraped from a 24–48 hour YEPD plate and washed in 1 ml water. Washed cells were resuspended in 400 μl of spheroplast buffer (1.2 M sorbitol, 10 mM Na citrate pH 7.5, 10 mM EDTA, 10 mM DTT, 1 mg/ml zymolyase 100T) and incubated at 37° C. for 10 minutes. Four hundred μl of 1% SDS was added, the cell suspension was mixed at room temperature until clear, 300 μl of 5 M potassium acetate was mixed in, and the mixture was clarified by microcentrifugation for 5 minutes. 750 μl of the clarified lysate was extracted with an equal volume of phenol:chloroform:isoamyl alcohol (25:24:1), 600 μl was transferred to a fresh tube, 2 volumes of 100% ethanol was added, and the DNA was precipitated by microcentrifugation for 15 minutes at 4° C. The pellet was resuspended in 50 μl of TE (10 mM Tris pH 8.0, 1 mM EDTA) containing 100 μg/ml of RNAase A. Ten μl of DNA (approximately 100 ng) was digested in 100 μl total volume with appropriate enzymes, precipitated with 200 μl ethanol, and resuspended in 10 μl of DNA loading dye. The DNA was separated in 0.7% agarose gels and transferred to nylon membranes (Nytran N+, Amersham Corp., Arlington Heights, Ill.) in a semi-dry blotting apparatus (BioRad Laboratories, Richmond, Calif.) as recommended by the manufacturer. Transferred DNA was denatured, neutralized, and cross-linked to the membrane with UV light using a Stratalinker (Stratagene, La Jolla, Calif.). To identify strains with a tandem integration at PEP4, two probes were used. One was a 1400 bp EcoRI—HindIII fragment from the 3' end of PEP4. The second was a 2000 bp BamHI—EcoRI fragment from the 5' end of PEP4. Fragments were detected using chemiluminescence reagents (ECL™ direct labelling kit; Amersham Corp., Arlington Heights, Ill.).

Parent strains harboring a tandem duplication of the wild-type and deletion alleles of the gene were grown in YEPD broth overnight to allow for the generation of looped-out, Ade strains. These cells were then plated at a density of 2000–5000 colonies per plate on adenine-limited YEPD plates, grown for 3 days at 30° C. and 3 days at room temperature. The shift to room temperature enhanced pigmentation of rare, pink, Ade colonies. Loop-out strains were consistently detected at a frequency of approximately one pink, Ade colony per 10,000 colonies screened.

These strains were screened for retention of the wild-type or mutant genes by Southern blotting or by PCR using primers that spanned the site of the deletion. An ade2–11 pep4Δ strain was designated PMAD15.

The PRB1 gene was then deleted from PMAD15 essentially as described above by transformation with plasmid pCZR153. Blots were probed with PCR—generated probes for internal portions of the PRB1 and ADE2 genes. The PRB1 probe was generated by subcloning a 2.6 kb ClaI—SpeI fragment of PRB1 into the phagemid vector pBluescript® II KS(+) to produce pCZR150, and amplifying the desired region by PCR using primers ZC447 (SEQ ID NO:17) and ZC976 (SEQ ID NO:18). The ADE2 probe was generated by amplifying the ADE2 gene in pCZR139 with primers ZC9079 (SEQ ID NO:19) and ZC9080 (SEQ ID NO:20). The resulting ade2–11 pep4Δ prb1Δ strain was designated PMAD16.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated DNA molecule of up to 1500 nucleotides in length comprising nucleotide 810 to nucleotide 1724 of SEQ ID NO: 1.

2. A DNA construct comprising the following operably linked elements:
   a first DNA segment comprising at least a portion of the sequence of SEQ ID NO: 1 from nucleotide 733 to nucleotide 1732, wherein said portion is a functional transcription promoter;
   a second DNA segment encoding a protein of interest other than a *Pichia methanolica* glyceraldehyde-3-phosphate dehydrogenase; and
   a third DNA segment comprising a transcription terminator.

3. The DNA construct of claim 2 wherein said first DNA segment is from 900 to 1500 nucleotides in length.

4. The DNA construct of claim 2 wherein the first DNA segment comprises nucleotide 810 to nucleotide 1724 of SEQ ID NO: 1.

5. The DNA construct of claim 2 wherein the first DNA segment is essentially free of DNA encoding a *Pichia methanolica* glyceraldehyde-3-phosphate dehydrogenase.

6. The DNA construct of claim 2, further comprising a selectable marker.

7. The DNA construct of claim 2, further comprising a secretory signal sequence operably linked to the first and second DNA segments.

8. The DNA construct of claim 7, wherein the secretory signal sequence is a *Saccharomyces cerevisiae* alpha-factor pre-pro sequence.

9. The DNA construct of claim 2 wherein said third DNA segment comprises a transcription terminator of a *Pichia methanolica* AUG1 or GAP1 gene.

10. The DNA construct of claim 9, wherein said terminator comprises nucleotides 2735 to 2795 of SEQ ID NO: 1.

11. A *Pichia methanolica* cell containing the DNA construct of claim 2.

12. The *Pichia methanolica* cell of claim 11 wherein the DNA construct is genomically integrated.

13. The *Pichia methanolica* cell of claim 12 wherein the DNA construct is genomically integrated in multiple copies.

14. The *Pichia methanolica* cell of claim 11 wherein the first DNA segment is from 900 to 1500 nucleotides in length.

15. The *Pichia methanolica* cell of claim 11 wherein the first DNA segment comprises nucleotide 810 to nucleotide 1724 of SEQ ID NO: 1.

16. The *Pichia methanolica* cell of claim 11, wherein the cell is functionally deficient in vacuolar proteases proteinase A and proteinase B.

17. A method of producing a protein of interest comprising:
   culturing the cell of claim 11 whereby the second DNA segment is expressed and the protein of interest is produced; and
   recovering the protein of interest.

18. The method of claim 17 wherein the DNA construct is genomically integrated in multiple copies.

19. The method of claim 17, wherein the cell is deficient in vacuolar proteases proteinase A and proteinase B.

20. A DNA construct comprising the following operably linked elements:
   a first DNA segment comprising a *Pichia methanolica* gene transcription promoter;
   a second DNA segment encoding a protein of interest other than a *Pichia methanolica* protein; and
   a third DNA segment comprising nucleotides 2735 to 2795 of SEQ ID NO: 1.

* * * * *

SEQUENCE LISTING

<160> NUMBER OF SEQ ID NOS: 20

<210> SEQ ID NO 1
<211> LENGTH: 4409
<212> TYPE: DNA
<213> ORGANISM: Pichia methanolica
<220> FEATURE:
<221> NAME/KEY: CDS
<222> LOCATION: (1733)...(2734)

<400> SEQUENCE: 1

```
cccgggggat cttattttct gcaagaactt aaccgaggga catgtcaaac caagcatact      60
gtaaaagaaa tagccgatgg tttatatata tatatacttg cgttagtaga aacagtttat     120
gcatgcatgg atgcaagaac tcagatatca ggttatcaag aaacatggag aaattcctaa     180
acagaaacgg aattaatccg aaattctcgg tctcccaaag aaaatagatg cacaagctaa     240
```

-continued

```
tacagcttgc taactagctt caactttcaa aaaaaattct aagctattga atattcatca      300
agataatagt ctatataaag atgtaaagtc attattattg ggatatataa acgtcctata      360
tattgctgaa atgttaggtg tatgtactga aaacaatcag tttgagttta ccagagagag      420
acgatggatc tacagatcaa tagagagaga ataagatgag aataagatga ttaatagtga      480
gaggtagtag ccactggcgg gaggatgaaa atatcccgga taaacttaga aagaaattaa      540
ttacacgtat aagtaacatt tgttattgtc gaatctcaga tcagttgatg cctggaacag      600
atcgacttat agatattatc agatcataat catgaggcga ggtgcgacta gtaccaggtg      660
atgatatatt gtttccggtt atttcaaata gttgacgtcg ttgtgtgatt gggaaggcgt      720
cggagtaaca gaaacagtaa cggtacaagc atcattatga gttgagggta tgtagggaag      780
cagttgtttg taagcatgtt tacaaatgca atgcatgtta cgattggact acaattaaat      840
ccgaatgtac ctatataacg tgttgtacgt gttgtgccgt aagtagcccg atactagatg      900
cttactacgt cactgatctg ttcggatctc agtccattca tgtgtcaaaa tagttagtag      960
ctaagggga tacaggaag atgtttggta cgattatcgg agggatgtgt cttctgaggg       1020
gggaggagag agggcgtgta aggagtttgt ttgtttgttt gtttgttgag agaagggggg     1080
gagaagaggg ggtggtgggc tgatggcaat tgatatagag ggagagtgtg cgttaactgt     1140
ttagtgtggt ggcggtacgg ggtacactgt agaggggac attataatgg ttatgtgtat      1200
atgctgtata tatgaataca agtagggagt gactacacat tgcaattgat aatatgtgta    1260
tgtgtgcgca tcagtatata cactcggagg ttctgaaagc catcattgta ttggacgttt    1320
gaatggtatt agatgacttg ttgtactaga ggacggagaa tgggtgagtg aagcaatag     1380
ataataatgg aaagtttgct cggtggtgga cattggcccg gagtagtgat accgtcacct   1440
taaaattgca gttaggggat gatgctccgg ggcacgacct gccaactaat ttaatagtcg   1500
tctaacgctg aacaggtgt tgttccacaa gtagatgagt ttgttggttg gctggtcaaa   1560
tgctgccttg atccatcgtt ttatatataa agactcactt ctcctcctct tgttcaattg   1620
tttcacactc aactgcttct cccttatctt ttttttttcc ctgttttatt ccccattgaa   1680
ctagatcaca tcttttcata ttacacactt ttatttatta taattacaca aa atg gct   1738
                                                           Met Ala
                                                             1
att aac gtt ggt att aac ggt ttc ggt aga atc ggt aga tta gtc ttg      1786
Ile Asn Val Gly Ile Asn Gly Phe Gly Arg Ile Gly Arg Leu Val Leu
        5                  10                  15
aga gtt gct tta tca aga aag gac atc aac att gtt gct gtc aat gat      1834
Arg Val Ala Leu Ser Arg Lys Asp Ile Asn Ile Val Ala Val Asn Asp
     20                  25                  30
cct ttc att gct gct gaa tac gct gct tac atg ttc aag tac gat tcc      1882
Pro Phe Ile Ala Ala Glu Tyr Ala Ala Tyr Met Phe Lys Tyr Asp Ser
 35                  40                  45                  50
act cac ggt aag tac gcc ggc gaa gtt tcc agt gac ggt aaa tac tta      1930
Thr His Gly Lys Tyr Ala Gly Glu Val Ser Ser Asp Gly Lys Tyr Leu
                 55                  60                  65
atc att gat ggt aag aag att gaa gtt ttc caa gaa aga gac cca gtt      1978
Ile Ile Asp Gly Lys Lys Ile Glu Val Phe Gln Glu Arg Asp Pro Val
             70                  75                  80
aac atc cca tgg ggt aaa gaa ggt gtc caa tac gtt att gac tcc act      2026
Asn Ile Pro Trp Gly Lys Glu Gly Val Gln Tyr Val Ile Asp Ser Thr
         85                  90                  95
ggt gtt ttc act acc ttg gct ggt gct caa aag cac att gat gcc ggt      2074
Gly Val Phe Thr Thr Leu Ala Gly Ala Gln Lys His Ile Asp Ala Gly
```

-continued

|  |  |  |  |  |  |  |  |  |  |  |  |  |  |  |  |
|---|---|---|---|---|---|---|---|---|---|---|---|---|---|---|---|
| | | 100 | | | | | 105 | | | | | 110 | | | |

```
gct gaa aag gtt atc atc act gct cca tct gct gat gct cca atg ttc    2122
Ala Glu Lys Val Ile Ile Thr Ala Pro Ser Ala Asp Ala Pro Met Phe
115             120             125             130 gtt gtt ggt gtt aac gaa aag gaa tac act tct gac ttg aag att gtt    2170
Val Val Gly Val Asn Glu Lys Glu Tyr Thr Ser Asp Leu Lys Ile Val
            135             140             145 tct aac gct tca tgt acc acc aac tgt ttg gct cca tta gct aag gtt    2218
Ser Asn Ala Ser Cys Thr Thr Asn Cys Leu Ala Pro Leu Ala Lys Val
        150             155             160 gtt aac gac aac ttt ggt att gaa tca ggt tta atg acc act gtc cac    2266
Val Asn Asp Asn Phe Gly Ile Glu Ser Gly Leu Met Thr Thr Val His
    165             170             175 tcc att acc gct acc caa aag acc gtc gat ggt cca tca cac aag gac    2314
Ser Ile Thr Ala Thr Gln Lys Thr Val Asp Gly Pro Ser His Lys Asp
180             185             190 tgg aga ggt ggt aga act gct tcc ggt aac att atc cca tca tct act    2362
Trp Arg Gly Gly Arg Thr Ala Ser Gly Asn Ile Ile Pro Ser Ser Thr
195             200             205             210 ggt gct gct aag gct gtt ggt aag gtt tta cct gtc tta gct ggt aag    2410
Gly Ala Ala Lys Ala Val Gly Lys Val Leu Pro Val Leu Ala Gly Lys
            215             220             225 tta acc ggt atg tct tta aga gtt cct act acc gat gtt tcc gtt gtt    2458
Leu Thr Gly Met Ser Leu Arg Val Pro Thr Thr Asp Val Ser Val Val
        230             235             240 gat tta acc gtt aac tta aag act cca acc act tac gaa gct att tgt    2506
Asp Leu Thr Val Asn Leu Lys Thr Pro Thr Thr Tyr Glu Ala Ile Cys
    245             250             255 gct gct atg aag aag gct tct gaa ggt gaa tta aag ggt gtt tta ggt    2554
Ala Ala Met Lys Lys Ala Ser Glu Gly Glu Leu Lys Gly Val Leu Gly
260             265             270 tac act gaa gac gct gtt gtt tcc act gat ttc tta acc gat aac aga    2602
Tyr Thr Glu Asp Ala Val Val Ser Thr Asp Phe Leu Thr Asp Asn Arg
275             280             285             290 tca tct atc ttt gat gct aag gct ggt atc tta tta acc cca act ttc    2650
Ser Ser Ile Phe Asp Ala Lys Ala Gly Ile Leu Leu Thr Pro Thr Phe
            295             300             305 gtt aag tta atc tct tgg tac gat aac gaa tac ggt tac tcc acc aga    2698
Val Lys Leu Ile Ser Trp Tyr Asp Asn Glu Tyr Gly Tyr Ser Thr Arg
        310             315             320 gtt gtt gat tta cta caa cac gtt gct tcc gct taa atcttacaat         2744
Val Val Asp Leu Leu Gln His Val Ala Ser Ala *
    325             330 ctagattgtg aagtataagt aagcaaaaat tatatatata tttgtctttc atagtataag  2804
tatagttttc atgagaaata cagataaaca acaaaaaata agttcttttt gaaaagtta   2864 gattttattc ttgaacttag taaaagcctt cctttacag ctgcttactt acaaccttga   2924
aggctattgc ataagctcaa ttgaaaacga gtataatata ctgatttcaa ggtttaatta  2984
tctgtaattt tcaagtactt ccatacgtgg aaacctccca caattaacag caacacgaaa  3044
catccatcat ccaacaaccg agatgcggat taggcccgga gagataatat ttttcggtgt  3104
ggcggtggtt tcaactccga acgcagcgca gccaaaagca aacagatgat ttagtgaact  3164
cttcttatga tagatttttg gctgattgag ttgatctgac ctgtgtggtt cgatcgaatt  3224
ctattgtgtt tgatgccctg gtagtggtgt gcttcatctt attgtgaagt gtgaatccta  3284
gcgattatgg catttggacg ccaactacta gctctgacgg tagtggcttc tacgaatgta  3344
acttacaatt ctgctcaatt cgaacatctt ttcagtaaga gaagttatat atgtatgtgt  3404
```

```
gtatgtgtat gtaaatatac ataaccgctt gtggggtga ttttggtttt gtactgatgt    3464
gaaactcagt gctatcggat gatgctgtca ccaacaacag ctgcttaacc ttcttttttac   3524 tattctgata cagaattagg aaagtttccg gatttgtgat gtgcggcttt ggttgccatt   3584
agtctccttt ttttggaggg aggagtgaag tggtgcgtta tgtgccctga tccaatggtt   3644
ttgaaagagg gagctaggga tagttaatgg gtagacctat gaacattgtg tattaatata   3704
ttgaaatata caaacataac ggctgaaaac agcaagaaat caaaaaggca caatttcaat   3764
ggtatataac ttcaataatg atagtaatag taatggtagt agttattaca ggaggaataa   3824
tatcaagaaa ggaaaactaa aagtacacca acgtattcag aaatacaaaa acagcgaaca   3884
aaatcgtcga ttagtaattc atatcatgat tgccatccaa acagctttct ttcattgaac   3944
tcacgagggc ttgcactatt ttccctgctt gatgagtaat ccatcatttc aaactcggtt   4004
gaacctgtag caccagaagc gccatttgac gtaattggcc ttgtaatttg ctgttgttgt   4064
tgggatatgt ttgattcatt ttggaaacgt tcatgatgcc ctcttttttt gttgtttgtt   4124
gttggtatcg gtgaattcga tctagatgca gaactgccac tattgttgtt attgccgttg   4184
ttcgcattat tgttatcgtc aaagtcaaag tcaagtaatg gaagaccaag ggaagcatca   4244
acaccaaaat cattcaacat cagtaaatcc gagtacgact taatggtatc tgcctgaatc   4304
gttgcttgct gctgattatg ctgttgttgg ttttgttgtt gctgtttcgc agtcagttgg   4364
aaatgatcca ctagttctag agcggccgcc accgcggtgg agctc              4409

<210> SEQ ID NO 2
<211> LENGTH: 3077
<212> TYPE: DNA
<213> ORGANISM: Pichia methanolica

<400> SEQUENCE: 2
cagctgctct gctccttgat tcgtaattaa tgttatcctt ttactttgaa ctcttgtcgg     60
tccccaacag ggattccaat cggtgctcag cgggatttcc catgaggttt ttgacaactt   120
tattgatgct gcaaaaactt ttttagccgg gtttaagtaa ctgggcaata tttccaaagg   180
ctgtgggcgt tccacactcc ttgcttttca taatctctgt gtattgtttt attcgcattt   240
tgattctctt attaccagtt atgtagaaag atcggcaaac aaaatatcaa ctttatctt    300 gaacgctgac ccacggtttc aaataactat cagaactcta tagctatagg ggaagtttac   360
tgcttgctta aagcggctaa aaagtgtttg gcaaattaaa aaagctgtga caagtaggaa   420
ctcctgtaaa gggccgattc gacttcgaaa gagcctaaaa acagtgacta ttggtgacgg   480
aaaattgcta aaggagtact agggctgtag taataaataa tggaacagtg gtacaacaat   540 aaagaatga cgctgtatgt cgtagcctgc acgagtagct cagtggtaga gcagcagatt    600
gcaaatctgt tggtcaccgg ttcgatccgg tctcgggctt cctttttgc ttttttcgata   660 tttgcgggta ggaagcaagg tctagttttc gtcgtttcgg atggtttacg aaagtatcag   720
ccatgagtgt ttccctctgg ctacctaata tatttattga tcggtctctc atgtgaatgt   780
ttctttccaa gttcggcttt cagctcgtaa atgtgcaaga atatttgac tccagcgacc     840 tttcagagtc aaattaattt tcgctaacaa tttgtgtttt tctggagaaa cctaaagatt   900
taactgataa gtcgaatcaa catctttaaa tcctttagtt aagatctctg cagcggccag   960
tattaaccaa tagcatattc acaggcatca catcggaaca ttcagaatgg actcgcaaac  1020
tgtcgggatt taggtggtg gccaacttgg tcgtatgatc gttgaagctg cacacagatt   1080
```

-continued

```
gaatatcaaa actgtgattc tcgaaaatgg agaccaggct ccagcaaagc aaatcaacgc    1140
tttagatgac catattgacg gctcattcaa tgatccaaaa gcaattgccg aattggctgc    1200
caagtgtgat gttttaaccg ttgagattga acatgttgac actgatgcgt tggttgaagt    1260
tcaaaaggca actggcatca aaatcttccc atcaccagaa actatttcat tgatcaaaga    1320
taaatacttg caaaagagc atttgattaa gaatggcatt gctgttgccg aatcttgtag     1380
tgttgaaagt agcgcagcat ctttagaaga agttggtgcc aaatacggct tcccatacat    1440
gctaaaatct gaacaatgg cctatgacg aagaggtaat tttgttgtca agacaagtc       1500 atatatacct gaagctttga aagttttaga tgacaggccg ttatacgccg agaaatgggc    1560
tccattttca aaggagttag ctgttatggt tgtgagatca atcgatggcc aagtttattc    1620
ctacccaact gttgaaacca tccaccaaaa caacatctgt cacactgtct ttgctccagc    1680
tagagttaac gatactgtcc aaaagaaggc ccaaattttg gctgacaacg ctgtcaaatc    1740
tttcccaggt gctggtatct ttggtgttga atgttttta ttacaaaatg gtgacttatt     1800
agtcaacgaa attgccccaa gacctcacaa ttctggtcac tataccatcg acgcttgtgt    1860
cacctcgcaa tttgaagctc atgttagggc cattactggt ctacccatgc cgaagaactt    1920
cacttgtttg tcgactccat ctacccaagc tattatgttg aacgttttag gtggcgatga    1980
gcaaaacggt gagttcaaga tgtgtaaaag agcactagaa actcctcatg cttctgttta    2040
cttatacggt aagactacaa gaccaggcag aaaaatgggt cacattaata tagtttctca    2100
atcaatgact gactgtgagc gtagattaca ttacatagaa ggtacgacta acagcatccc    2160
tctcgaagaa cagtacacta cagattccat tccgggcact tcaagcaagc cattagtcgg    2220
tgtcatcatg ggttccgatt cggacctacc agtcatgtct ctaggttgta atatattgaa    2280
gcaatttaac gttccatttg aagtcactat cgtttccgct catagaaccc cacaaagaat    2340
ggccaagtat gccattgatg ctccaaagag agggttgaag tgcatcattg ctggtgctgg    2400
tggtgccgct catttaccgg gaatggttgc ggcgatgacg ccgctgcctg ttattggtgt    2460
ccctgttaaa ggctctactt tggatggtgt tgattcacta cactccatcg ttcaaatgcc    2520
aagaggtatt cctgttgcta ctgtggctat taacaatgct actaacgctg ccttgctagc    2580
tatcacaatc ttaggtgccg gcgatccaaa tacttgtctg caatggaagt ttatatgaac    2640
aatatggaaa atgaagtttt gggcaaggct gaaaaattgg aaaatggtgg atatgaagaa    2700
tacttgagta catacaagaa gtagaacctt ttatatttga tatagtactt actcaaagtc    2760
ttaattgttc taactgttaa tttctgcttt gcatttctga aagtttaag acaagaaatc     2820 ttgaaatttc tagttgctcg taagaggaaa cttgcattca aataacatta acaataaatg    2880
acaataatat attatttcaa cactgctata tggtagtttt ataggtttgg ttaggatttg    2940
agatattgct agcgcttatc attatcctta attgttcatc gacgcaaatc gacgcatttc    3000
cacaaaaatt ttccgaacct gttttcact tctccagatc ttggtttagt atagcttttg     3060
acacctaata cctgcag                                                   3077
```

<210> SEQ ID NO 3
<211> LENGTH: 19
<212> TYPE: DNA
<213> ORGANISM: Artificial Sequence
<220> FEATURE:
<223> OTHER INFORMATION: Oligonucleotide primer ZC11,356

<400> SEQUENCE: 3
ttacatgttc aagtacgat                                                 19

<210> SEQ ID NO 4
<211> LENGTH: 18
<212> TYPE: DNA
<213> ORGANISM: Artificial Sequence
<220> FEATURE:
<223> OTHER INFORMATION: Oligonucleotide primer ZC11,357

<400> SEQUENCE: 4
tgatttcatc gtaagtgg                                              18

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer ZC11,733

<400> SEQUENCE: 5
atcccatggg gtaaagaagg                                            20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide primer ZC11,734

<400> SEQUENCE: 6
ataccggtta acttaccagc                                            20

<210> SEQ ID NO 7
<211> LENGTH: 29
<212> TYPE: DNA
<213> ORGANISM: Artificial Sequence
<220> FEATURE:
<223> OTHER INFORMATION: Oligonucleotide primer ZC12,586

<400> SEQUENCE: 7
ggtgcggccg caatgcatgt tacgattgg                                  29

<210> SEQ ID NO 8
<211> LENGTH: 45
<212> TYPE: DNA
<213> ORGANISM: Artificial Sequence
<220> FEATURE:
<223> OTHER INFORMATION: Oligonucleotide primer ZC12,565

<400> SEQUENCE: 8
ctagataaaa gagaagaaga gccaaagact ccacaaaaca ttgca                45

<210> SEQ ID NO 9
<211> LENGTH: 17
<212> TYPE: DNA
<213> ORGANISM: Artificial Sequence
<220> FEATURE:
<223> OTHER INFORMATION: Oligonucleotide primer ZC9118

<400> SEQUENCE: 9
acctcccagt aagcctt                                               17

<210> SEQ ID NO 10
<211> LENGTH: 17
<212> TYPE: DNA
<213> ORGANISM: Artificial Sequence
<220> FEATURE:

-continued

```
<223> OTHER INFORMATION: Oligonucleotide primer ZC9464
<221> NAME/KEY: misc_feature
<222> LOCATION: (1)...(17)
<223> OTHER INFORMATION: n = A,T,C or G

<400> SEQUENCE: 10
ttyggnaart tygaygg                                                  17

<210> SEQ ID NO 11
<211> LENGTH: 421
<212> TYPE: DNA
<213> ORGANISM: Pichia methanolica
<220> FEATURE:
<221> NAME/KEY: CDS
<222> LOCATION: (2)...(421)

<400> SEQUENCE: 11 g gaa ggt aac gtt tct cag gat act tta gct tta ggt gat tta gtt att    49
  Glu Gly Asn Val Ser Gln Asp Thr Leu Ala Leu Gly Asp Leu Val Ile
    1               5                  10                  15 cca aaa caa gac ttt gcc gaa gct act tct gag cca ggt tta gca ttc     97
Pro Lys Gln Asp Phe Ala Glu Ala Thr Ser Glu Pro Gly Leu Ala Phe
             20                  25                  30 gca ttt ggt aaa ttt gat ggt att tta ggt tta gct tac gat agc att    145
Ala Phe Gly Lys Phe Asp Gly Ile Leu Gly Leu Ala Tyr Asp Ser Ile
         35                  40                  45 tcg gtc aac aag att gtt cct cct att tat aat gct tta aac ttg ggt    193
Ser Val Asn Lys Ile Val Pro Pro Ile Tyr Asn Ala Leu Asn Leu Gly
     50                  55                  60 tta tta gat gaa cct caa ttt gcc ttc tac cta ggt gat act aac acc    241
Leu Leu Asp Glu Pro Gln Phe Ala Phe Tyr Leu Gly Asp Thr Asn Thr
 65                  70                  75                  80 aat gaa gaa gat ggt ggt ctt gcc act ttt ggt ggt gtt gat gag tcc    289
Asn Glu Glu Asp Gly Gly Leu Ala Thr Phe Gly Gly Val Asp Glu Ser
                 85                  90                  95 aag tat act ggt aaa gtt aca tgg tta cca gtc aga aga aag gct tac    337
Lys Tyr Thr Gly Lys Val Thr Trp Leu Pro Val Arg Arg Lys Ala Tyr
            100                 105                 110 tgg gaa gtt tca tta gac ggt att tca tta ggt gat gaa tac gcg cca    385
Trp Glu Val Ser Leu Asp Gly Ile Ser Leu Gly Asp Glu Tyr Ala Pro
        115                 120                 125 tta gaa ggc cat gga gct gcc att gat aca ggt acc                    421
Leu Glu Gly His Gly Ala Ala Ile Asp Thr Gly Thr
    130                 135                 140

<210> SEQ ID NO 12
<211> LENGTH: 140
<212> TYPE: PRT
<213> ORGANISM: Pichia methanolica

<400> SEQUENCE: 12

Glu Gly Asn Val Ser Gln Asp Thr Leu Ala Leu Gly Asp Leu Val Ile
  1               5                  10                  15

Pro Lys Gln Asp Phe Ala Glu Ala Thr Ser Glu Pro Gly Leu Ala Phe
             20                  25                  30

Ala Phe Gly Lys Phe Asp Gly Ile Leu Gly Leu Ala Tyr Asp Ser Ile
         35                  40                  45

Ser Val Asn Lys Ile Val Pro Pro Ile Tyr Asn Ala Leu Asn Leu Gly
     50                  55                  60

Leu Leu Asp Glu Pro Gln Phe Ala Phe Tyr Leu Gly Asp Thr Asn Thr
 65                  70                  75                  80
```

```
Asn Glu Glu Asp Gly Gly Leu Ala Thr Phe Gly Gly Val Asp Glu Ser
                85                  90                  95

Lys Tyr Thr Gly Lys Val Thr Trp Leu Pro Val Arg Arg Lys Ala Tyr
            100                 105                 110

Trp Glu Val Ser Leu Asp Gly Ile Ser Leu Gly Asp Glu Tyr Ala Pro
        115                 120                 125

Leu Glu Gly His Gly Ala Ala Ile Asp Thr Gly Thr
    130                 135                 140

<210> SEQ ID NO 13
<211> LENGTH: 17
<212> TYPE: DNA
<213> ORGANISM: Artificial Sequence
<220> FEATURE:
<223> OTHER INFORMATION: Oligonucleotide primer ZC9126

<400> SEQUENCE: 13
atgtcaacac atttacc                                                    17

<210> SEQ ID NO 14
<211> LENGTH: 17
<212> TYPE: DNA
<213> ORGANISM: Artificial Sequence
<220> FEATURE:
<223> OTHER INFORMATION: Oligonucleotide primer ZC9741
<221> NAME/KEY: misc_feature
<222> LOCATION: (1)...(17)
<223> OTHER INFORMATION: n = A,T,C or G

<400> SEQUENCE: 14
cayggnacnc aytgygc                                                    17

<210> SEQ ID NO 15
<211> LENGTH: 368
<212> TYPE: DNA
<213> ORGANISM: Pichia methanolica
<220> FEATURE:
<221> NAME/KEY: CDS
<222> LOCATION: (1)...(366)
<221> NAME/KEY: misc_feature
<222> LOCATION: (1)...(368)
<223> OTHER INFORMATION: n = A,T,C or G

<400> SEQUENCE: 15 ggg tcc gna cnc atg gtg ttt cta aga att gcc cac att gtt gcc gtc      48
Gly Ser Xaa Xaa Met Val Phe Leu Arg Ile Ala His Ile Val Ala Val
1               5                   10                  15 aaa gtt tta aga tct aac ggt tca ggt tct atg ccc gat gtt gtc aag      96
Lys Val Leu Arg Ser Asn Gly Ser Gly Ser Met Pro Asp Val Val Lys
            20                  25                  30 ggt gtt gaa tat gct ccc aat gct cac ctt gcg gaa gcc aag gct aac     144
Gly Val Glu Tyr Ala Pro Asn Ala His Leu Ala Glu Ala Lys Ala Asn
        35                  40                  45 aag agt ggt ttt aaa ggt tct acc gcg aac atg tca tta ggt ggt ggt     192
Lys Ser Gly Phe Lys Gly Ser Thr Ala Asn Met Ser Leu Gly Gly Gly
    50                  55                  60 aaa tct cca gct tta gat atg tct gtt aac gct cct gtt aaa gca ggt     240
Lys Ser Pro Ala Leu Asp Met Ser Val Asn Ala Pro Val Lys Ala Gly
65                  70                  75                  80 tta cac ttt gcc gtt acc gct ggt aac gat aac act gat gca tgt aac     288
Leu His Phe Ala Val Thr Ala Gly Asn Asp Asn Thr Asp Ala Cys Asn
                85                  90                  95 tat tct cca gcc act act gaa aat act gtc act gtt gtt gct tcc act     336
Tyr Ser Pro Ala Thr Thr Glu Asn Thr Val Thr Val Val Ala Ser Thr
```

```
                     100                 105                 110
tta tct gat tcg aga gct gac atg tct aac tc                               368
Leu Ser Asp Ser Arg Ala Asp Met Ser Asn
        115                 120

<210> SEQ ID NO 16
<211> LENGTH: 122
<212> TYPE: PRT
<213> ORGANISM: Pichia methanolica
<220> FEATURE:
<221> NAME/KEY: VARIANT
<222> LOCATION: (1)...(122)
<223> OTHER INFORMATION: Xaa = Any Amino Acid

<400> SEQUENCE: 16

Gly Ser Xaa Xaa Met Val Phe Leu Arg Ile Ala His Ile Val Ala Val
  1               5                  10                  15

Lys Val Leu Arg Ser Asn Gly Ser Gly Ser Met Pro Asp Val Val Lys
             20                  25                  30

Gly Val Glu Tyr Ala Pro Asn Ala His Leu Ala Glu Ala Lys Ala Asn
         35                  40                  45

Lys Ser Gly Phe Lys Gly Ser Thr Ala Asn Met Ser Leu Gly Gly Gly
     50                  55                  60

Lys Ser Pro Ala Leu Asp Met Ser Val Asn Ala Pro Val Lys Ala Gly
 65                  70                  75                  80

Leu His Phe Ala Val Thr Ala Gly Asn Asp Asn Thr Asp Ala Cys Asn
                 85                  90                  95

Tyr Ser Pro Ala Thr Thr Glu Asn Thr Val Thr Val Val Ala Ser Thr
            100                 105                 110

Leu Ser Asp Ser Arg Ala Asp Met Ser Asn
        115                 120

<210> SEQ ID NO 17
<211> LENGTH: 17
<212> TYPE: DNA
<213> ORGANISM: Artificial Sequence
<220> FEATURE:
<223> OTHER INFORMATION: Oligonucleotide primer ZC447

<400> SEQUENCE: 17
taacaatttc acacagg                                                        17

<210> SEQ ID NO 18
<211> LENGTH: 18
<212> TYPE: DNA
<213> ORGANISM: Artificial Sequence
<220> FEATURE:
<223> OTHER INFORMATION: Oligonucleotide primer ZC976

<400> SEQUENCE: 18
cgttgtaaaa cgacggcc                                                       18

<210> SEQ ID NO 19
<211> LENGTH: 39
<212> TYPE: DNA
<213> ORGANISM: Artificial Sequence
<220> FEATURE:
<223> OTHER INFORMATION: Oligonucleotide primer ZC9079

<400> SEQUENCE: 19
cagctgccta ggactagttt cctcttacga gcaactaga                                39
```

```
<210> SEQ ID NO 20
<211> LENGTH: 38
<212> TYPE: DNA
<213> ORGANISM: Artificial Sequence
<220> FEATURE:
<223> OTHER INFORMATION: Oligonucleotide primer ZC9080

<400> SEQUENCE: 20
tgatcaccta ggactagtga caagtaggaa ctcctgta                                   38
```